US009443709B2

(12) United States Patent
Allsworth et al.

(10) Patent No.: US 9,443,709 B2
(45) Date of Patent: Sep. 13, 2016

(54) CORONA IONIZATION DEVICE AND METHOD

(71) Applicants: Max Allsworth, London (GB); Matthew Hart, London (GB); John Somerville, Royston (GB)

(72) Inventors: Max Allsworth, London (GB); Matthew Hart, London (GB); John Somerville, Royston (GB)

(73) Assignee: Owlstone Limited, Cambridge (GB)

( * ) Notice: Subject to any disclaimer, the term of this patent is extended or adjusted under 35 U.S.C. 154(b) by 0 days.

(21) Appl. No.: 14/355,481

(22) PCT Filed: Nov. 16, 2012

(86) PCT No.: PCT/IB2012/002856
§ 371 (c)(1),
(2) Date: Apr. 30, 2014

(87) PCT Pub. No.: WO2013/144679
PCT Pub. Date: Oct. 3, 2013

(65) Prior Publication Data
US 2014/0299759 A1    Oct. 9, 2014

Related U.S. Application Data

(60) Provisional application No. 61/560,592, filed on Nov. 16, 2011.

(51) Int. Cl.
*H01J 49/16*    (2006.01)
(52) U.S. Cl.
CPC .................... *H01J 49/168* (2013.01)
(58) Field of Classification Search
CPC .................................................. H01J 49/168
See application file for complete search history.

(56) References Cited

U.S. PATENT DOCUMENTS

| 5,153,892 | A  | * | 10/1992 | Kawakubo et al. | ............ 372/87 |
| 6,168,689 | B1 | * | 1/2001  | Park et al.     | ............ 204/164 |
| 6,414,978 | B2 | * | 7/2002  | Bragin et al.   | ............ 372/58 |
| 6,646,257 | B1 | * | 11/2003 | Fischer et al.  | ............ 250/288 |
| 6,654,402 | B1 | * | 11/2003 | Kakizaki et al. | ............ 372/86 |

(Continued)

FOREIGN PATENT DOCUMENTS

JP    2004186310 A  *  7/2004  ............. H01S 3/977

OTHER PUBLICATIONS

Adamov et al., "Characterization of a high resolution drift tube ion mobility spectrometer with a multi-ion source platform", International Journal of Mass Spectrometry 298 (2010) 24-29.*

*Primary Examiner* — Michael Logie
(74) *Attorney, Agent, or Firm* — Locke Lord LLP; Barry Kramer; Christopher J. Capelli

(57) ABSTRACT

A corona discharge ionizer device which emits ions generated by corona discharge to a gas flow to be ionized includes a discharge electrode having a pin configured tip portion. A second grid electrode positioned at a spaced distance from the discharge electrode is provided. The grid electrode is preferably formed from a sheet configured material which has at least one hole formed therein adapted and configured to permit the gas flow to pass therethrough. A power supply is coupled to the discharge electrode and grid electrode configured cause ion emission from the discharge electrode. The power supply is preferably an alternating current power supply configured to produce an alternating electric field region in close proximity to the tip portion of the discharge electrode sufficient to cause avalanche breakdown in the gas flowing in close proximity to the tip portion of the discharge electrode.

57 Claims, 12 Drawing Sheets

(56) References Cited

U.S. PATENT DOCUMENTS

| | | | |
|---|---|---|---|
| 7,002,146 B2* | 2/2006 | Fischer et al. | 250/288 |
| 7,112,785 B2* | 9/2006 | Laramee et al. | 250/288 |
| 7,820,979 B2* | 10/2010 | Belyakov et al. | 250/423 R |
| RE43,078 E* | 1/2012 | Cody et al. | 250/288 |
| 2004/0129876 A1* | 7/2004 | Franzen | 250/288 |
| 2005/0056776 A1* | 3/2005 | Willoughby et al. | 250/281 |
| 2006/0255261 A1* | 11/2006 | Whitehouse et al. | 250/288 |
| 2007/0007448 A1* | 1/2007 | Wang | 250/288 |
| 2007/0114395 A1* | 5/2007 | Swenson et al. | 250/292 |
| 2007/0138406 A1* | 6/2007 | Mordehai | 250/426 |
| 2011/0049352 A1* | 3/2011 | Ding et al. | 250/282 |
| 2011/0056371 A1* | 3/2011 | Koehl | 95/78 |
| 2011/0266433 A1* | 11/2011 | Jarrell | 250/282 |
| 2012/0012871 A1* | 1/2012 | Hsia | H01L 33/0079 257/98 |
| 2012/0312980 A1* | 12/2012 | Whitehouse | 250/282 |

* cited by examiner

CORONA IONIZATION DEVICE AND METHOD

RELATED APPLICATIONS

This application claims the benefit of U.S. Provisional Application No. 61/560,592, filed Nov. 16, 2011 the entire contents of which is expressly incorporated herein by reference.

GOVERNMENT LICENSE RIGHTS

This invention was made with Government support under HDTRA1-08-C-0010 awarded by the Defense Threat Reduction Agency. The Government has certain rights in the invention.

FIELD OF THE INVENTION

The present invention relates to devices and methods for generating ions. More specifically, the invention relates to devices and methods for generating ions using a corona discharge.

BACKGROUND OF THE INVENTION

The ability to ionize gases is useful for a wide range of applications including many chemical detection applications. Ionization techniques, in which a gas sample is ionized and then separated into constituent parts that can be detected individually, are widely used for gas composition sensing. Two well-known examples are Ion Mobility Spectrometry (IMS) and Field Asymmetric Ion Mobility Spectrometry (FAIMS), also known as Differential Mobility Spectrometry (DMS). Ion mobility detection techniques tend to be very well suited to measuring trace constituents of gas mixtures that often consist of a carrier gas with additional gases mixed in at low concentrations (for example part-per-million or part-per-billion levels). Ion mobility techniques can also be used effectively over a range of gas pressures, including pressures close to one atmosphere. This makes them useful for, amongst other things, measuring low-level impurities in air. Because they work by measuring properties of ionized molecules and because gas samples for analysis generally consist mainly of neutral molecules, ion-mobility-based detectors generally incorporate an ionizer. The sample gas is passed through the ionizer to produce a population of ionized molecules that are then manipulated in some way involving separation or selection of ionized molecules according to their behavior in an electric field, before being detected. Ionizers commonly in use include radioactive sources, light-based devices such as ultra-violet lamps, and electrostatic devices such as corona discharge ionizers.

Radioactive sources have long been used as ionizers for chemical detection systems. It is noted radioactive isotopes such as $^{241}$Am or $^{63}$Ni are commonly used as ionization sources to generate ions in a surrounding gas stream. Advantages of radioactive sources as ionizers include stable and well-understood ion chemistry and the ability to ionize without an external power source. A major drawback, however, is that radioactive sources pose a health hazard and are therefore not suitable for use in many applications and are subject to strict government regulation. Non-radioactive ionizers, including corona discharge ionizers, do not suffer from this disadvantage and can be widely and safely deployed in a range of applications.

A commonly used ion source in the field of chemical detection is the radioactive isotope $^{63}$Ni. The interactions of ionizing radiation emitted by $^{63}$Ni with many types of gas molecules have been studied and understood, meaning that the ion species produced when a $^{63}$Ni source ionizes a gas mixture of a given composition can generally be predicted with high confidence. $^{63}$Ni can therefore be thought of as a "reference" ionizer for many gas detection systems. Radioactive ionization sources have the advantage of simplicity, compactness, durability, and reliability. The regulations associated with these radioactive ionization sources, however, may render the incorporation of radioactive isotopes into a product commercially unfeasible. Therefore, there exists a need for an ionizer that has similar ionization properties to $^{63}$Ni but that does not suffer from the safety and regulatory drawbacks associated with radioactive sources.

It is also to be appreciated that electric field ionization has the advantage of a relatively simple design, relatively simple fabrication, and low power consumption. For instance, in electric field ionization, a large electric field typically between $10^7$ to $10^8$ V/m is generated between two electrodes. The large magnitude of the electric field accelerates any ions or other free charges within the field thereby causing the accelerated ions or other charges to collide with surrounding gas molecules. The collision of an accelerated ion or other charged particle (such as an electron) and a gas molecule creates an ionized molecule. A corona discharge is a type of electric field ionization where a neutral fluid such as, for example, air is ionized near an electrode having a high electric potential gradient. Such a potential gradient is achieved by using a discharge electrode having a small radius of curvature. The polarity of the discharge electrode determines whether the corona is a positive or negative corona. Typically, the corona has a plasma region and a unipolar region. In the plasma region, electrons avalanche to create more electron/ion pairs. In the unipolar region, the slowly moving massive (relative to the electron mass) ions move to the passive electrode, which is usually grounded. If the plasma region grows to encompass the passive electrode, a momentary spark or a continuous arc may occur. The spark or arc may damage the electrodes, produce contaminant ions, and reduce the lifetime of the ionization source. Therefore, there remains a need for devices and methods providing improved ionization.

SUMMARY OF THE INVENTION

In one aspect, a corona discharge ionizer device which emits ions generated by corona discharge to a gas flow to be ionized is described in which an aspect of the corona discharge ionizer device includes a discharge electrode having a pin configured tip portion. A second grid electrode is positioned at a spaced distance from the discharge electrode. The second electrode is preferably formed from a sheet configured material which has at least one hole formed therein adapted and configured to permit the gas flow to pass therethrough. A power supply is coupled to the discharge electrode and the second electrode configured to cause ion emission from the vicinity of the discharge electrode. The power supply is preferably an alternating current power supply configured to produce an alternating electric field region in close proximity to the tip portion of the discharge electrode sufficient to cause avalanche breakdown in the gas flowing in close proximity to the tip portion of the discharge electrode. The alternating current power supply produces free electrons, negative ions and positive ions such that when the discharge electrode is caused to repel positive ions, negatively charged bodies from the gas flow are caused to be directed towards the pin configured tip portion of the discharge electrode and positively charged bodies from the gas flow are caused to be directed towards the second electrode. Conversely, when the discharge electrode is caused to repel negative ions, positively charged bodies from the gas flow are caused to be directed towards the pin configured tip portion of the discharge electrode and negatively charged bodies from the gas flow are caused to be directed towards the second electrode.

In further optional aspects, a corona discharge ionizer which emits ions generated by corona discharge to a gas flow to be ionized is described in which an aspect of the corona discharge ionizer device includes a light source adapted and configured to provide an ultra-violet (UV) output creating seed ions or other free charges in the gas flow.

In a further aspect, a corona discharge ionizer which emits ions generated by corona discharge to a gas flow to be ionized is described which includes a discharge electrode having a pin configured tip portion wherein the discharge electrode has a hollowed body portion. A second electrode is positioned at a spaced distance from the discharge electrode. A power supply is coupled to the discharge electrode and the second electrode configured to cause ion generation from the vicinity of the discharge electrode. An ultra-violet (UV) light-emitting element is disposed in the hollowed body portion of the discharge electrode adapted and configured to provide a UV light output from the discharge electrode creating seed ions in the gas flow surrounding the discharge electrode.

In still another aspect, a corona discharge ionizer which emits ions generated by corona discharge to a gas flow to be ionized is described which includes a discharge electrode having a pin configured tip portion and a second electrode positioned at a spaced distance from the discharge electrode. An AC power supply and a method of creating a variable DC offset are coupled between the discharge electrode and the second electrode. The method of creating the DC offset can include a capacitor and/or a power supply between the discharge electrode and/or the second electrode whereby a mode balancing DC offset voltage is provided between the discharge electrode and the second electrode.

BRIEF DESCRIPTION OF THE DRAWINGS

The objects and features of the invention can be understood with reference to the following detailed description of an illustrative embodiment of the present invention taken together in conjunction with the accompanying drawings in which.

WRITTEN DESCRIPTION OF CERTAIN EMBODIMENTS OF THE INVENTION

Figure 1:
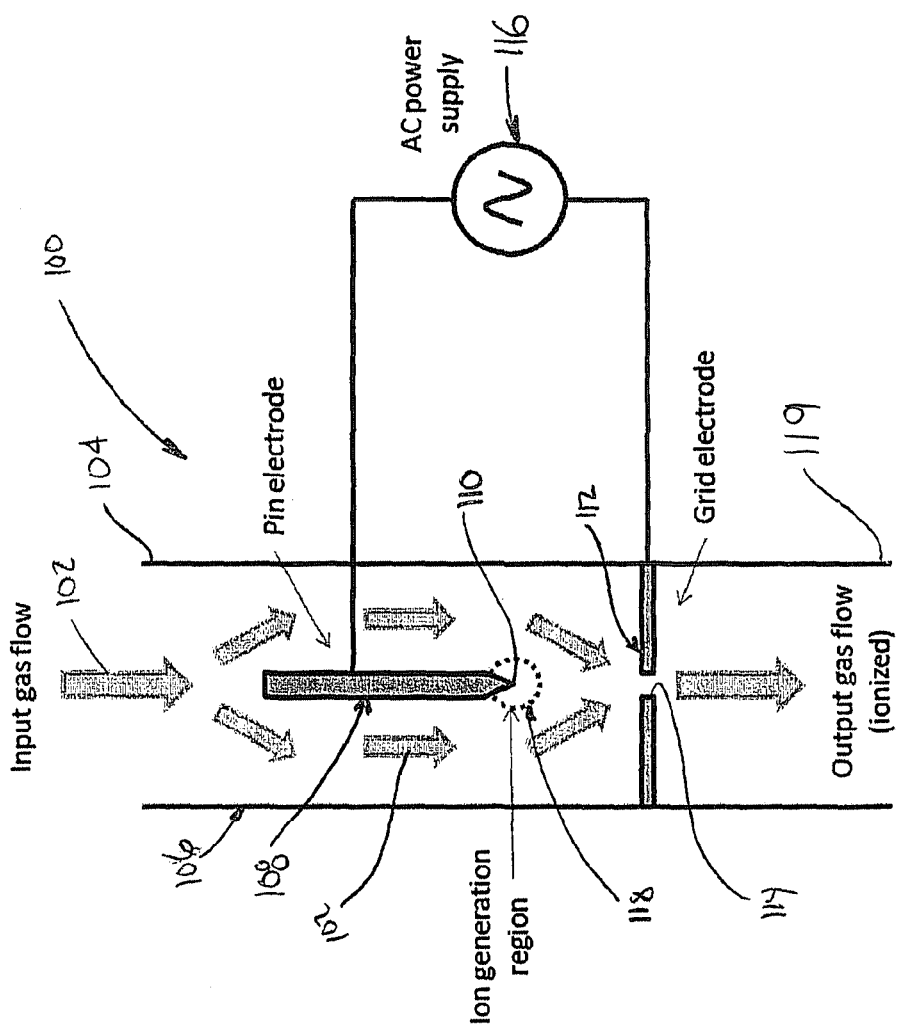
FIG. 1 is an illustrated embodiment of the invention depicting a corona ionizer.

The present invention is now described more fully with reference to the accompanying drawings, in which an illustrated embodiment of the present invention is shown wherein like reference numerals depict like elements. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Starting with reference to FIG. 1, shown is an illustrated embodiment of the invention depicting a corona discharge ionizer device 100. As illustrated, gas 102 flows in into the device 100 at an entry portion 104 of the gas tube 106 for the device 100, and flows around a pin electrode 108. It is to be understood and appreciated that the pin electrode 108 (e.g., a discharge electrode) has a moderately sharp tip 110 preferably configured to have a radius of curvature in the range 10-200 microns. Downstream in the gas flow 102 of the pin electrode 108 is a grid electrode 112. The grid electrode 112 is preferably formed from a metal sheet (but it is not to be understood to be limited thereto) having one or more holes 114 formed therethrough, each configured and adapted to permit gas 102 to flow therethrough.

It is to be understood and appreciated that the separation between the pin electrode 108 and the grid electrode 112 is a parameter that affects ionization performance for device 100. An exemplary separation between the pin 108 and the grid electrode 112 is 0.5 to 4 mm.

As illustrated in FIG. 1, the pin electrode 108 and grid electrode 112 are each preferably electrically coupled to an alternating current power supply 116 adapted and configured to apply an oscillating voltage between the pin electrode 108 and grid electrode 112. In accordance with the illustrated embodiment of the device 100, the oscillation frequency of the alternating current power supply 116 is typically in the range 10 to 100 kHz and the AC zero-to-peak voltage is typically in the range 1 to 5 kV. It is to be understood operation of the aforesaid alternating current power supply 116 is not to be understood to be limited to aforementioned operating values.

It is to be understood the high voltage AC signal applied between pin electrode 108 and grid electrode 112, via the alternating current power supply 116, in combination with the tip 110 of the pin electrode 108, produces a region of high alternating electric field 118 in close proximity to the tip 110 of the pin electrode 108 (the corona region). Within this region, the electric field reaches values high enough to cause avalanche breakdown in the gas 102, producing separated positive and negative charges, which in other words is a mixture of free electrons, negative ions and positive ions.

Figure 2:
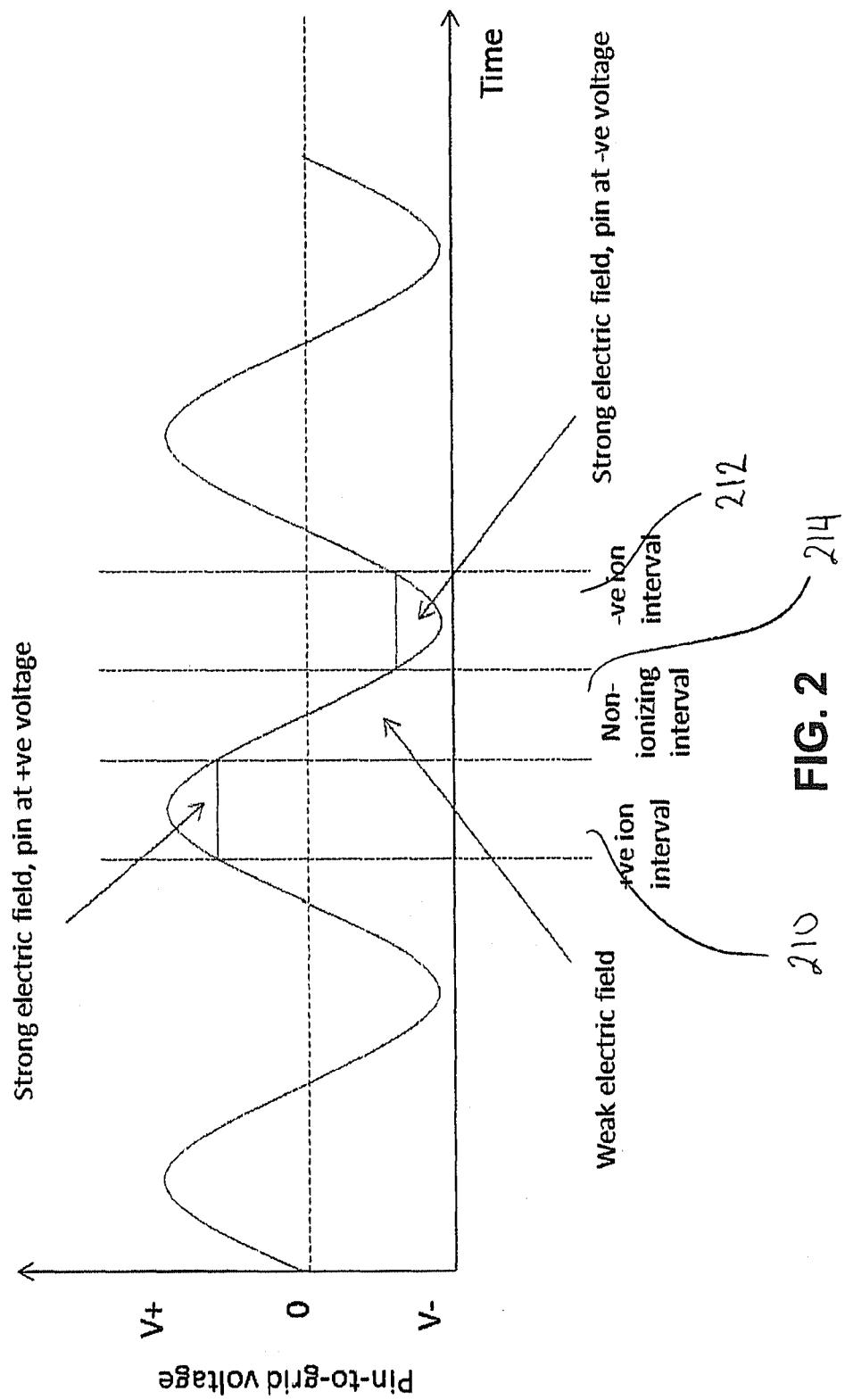
FIG. 2 depicts an exemplary corona drive waveform for the ionizer of FIG. 1.

With reference now to FIG. 2 (and with continuing reference to FIG. 1), the oscillation period of the alternating current power supply 116 is shown divided into three intervals: a "positive ion interval" 210 during which the pin electrode 108 is at a high positive voltage with respect to grid electrode 112, a "negative ion interval" 212 during which the pin electrode 108 is at a high negative voltage with respect to the grid electrode 112, and a "non-ionizing interval" 214 during which the voltage between the pin electrode 108 and grid electrode 112 is such that the electric field in region 118 is not high enough to produce ionization of the gas flow 102.

It is to be appreciated that during the positive ion interval 210 there is a strong electric field in the region 118 in close proximity to the tip 110 of the pin electrode 108, leading to avalanche breakdown of the nearby gas flow 102 causing generation of positive ions, free electrons and negative ions. It is noted the strong electric field drives negatively charged bodies very rapidly towards the conductive tip 110 of the pin electrode 108, where their excess charge is carried away via the conductor of the pin electrode 108. Conversely, positively charged bodies are thus driven rapidly away from the tip 110 of the pin electrode 108 towards the region of lower electric field in closer proximity to the grid electrode 112. Hence, during the positive ion interval 210, both positive and negative free charges (ions and electrons) are generated, but only positive ions can escape the high-field region 118 in close proximity to the tip 110 of the pin electrode 108.

During the negative ion interval 212 produced via AC power supply 116, the opposite of the positive ion interval 210 occurs. Again, both positive and negative free charges are generated from the gas flow 102, but the positive charges (ions) are rapidly driven into the pin electrode 108, which is now at a high negative voltage with respect to the grid electrode 112. The negative charges (ions and free electrons) can escape towards the lower-field regions in close proximity to the grid electrode 112.

And during the non-ionizing interval, the electric field produced via AC power supply 116 surrounding the pin electrode 108 is not strong enough to create avalanche breakdown of the gas flow 102, thus no ionization occurs. It is noted that existing free charges are, however, still swept either toward or away from the pin electrode 108 according to their polarity and the polarity of the voltage of the pin electrode 108.

It is to be further appreciated the above mentioned transition between periods when positive ions can escape the ionization region and periods when negative ions can escape occurs repeatedly and rapidly—typically at a frequency of approximately 30 kHz (the frequency at which the AC power supply 116 operates). Thus, a result is creation of a cloud of free positive and negative charges in and around the ionization region 118.

Figure 3:
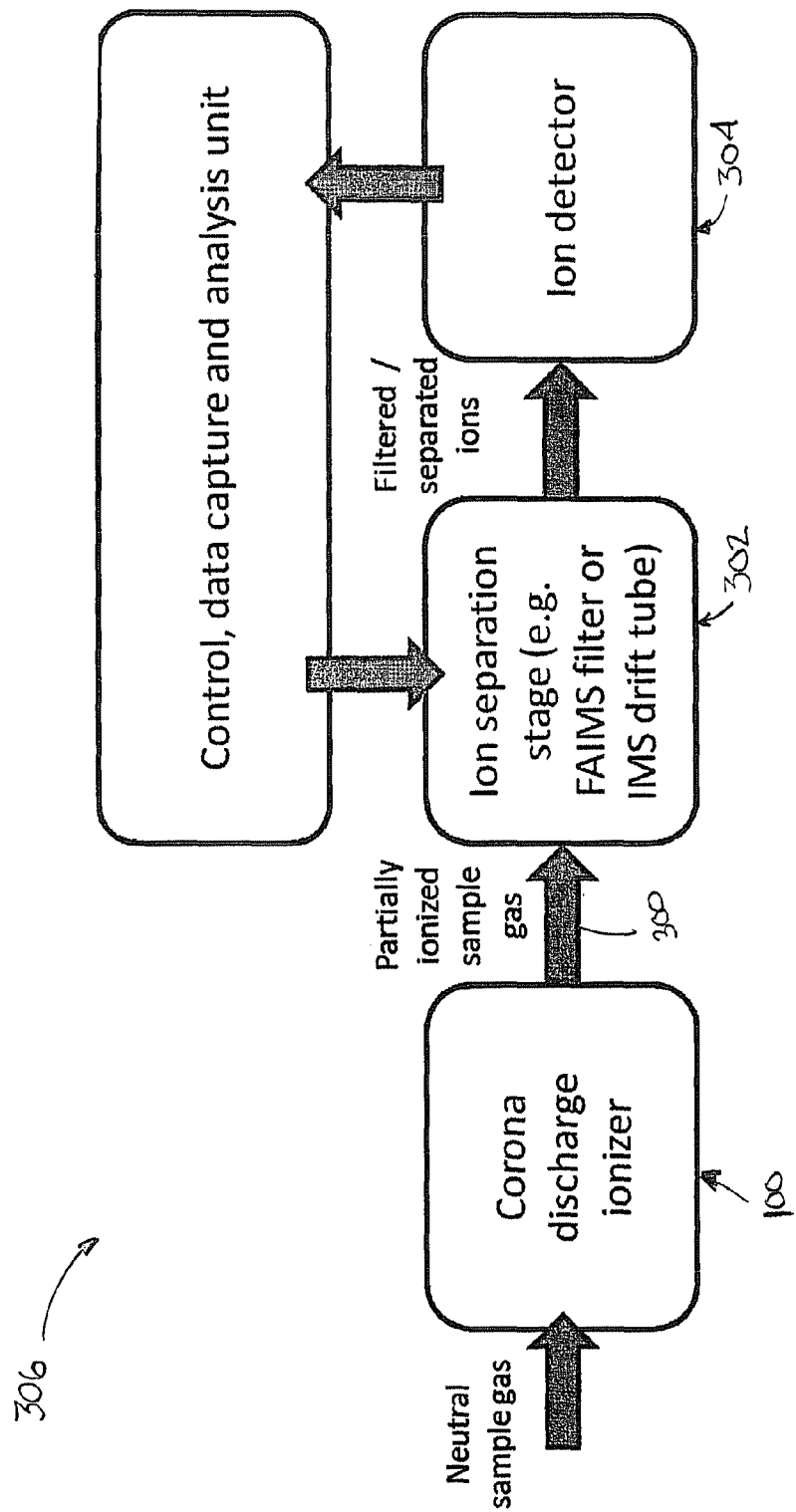
FIG. 3 depicts a schematic representation of a chemical spectrometer using the corona ionizer of FIG. 1.

In accordance with the above descriptions of FIGS. 1 and 2, and with reference now to FIG. 3, when the effect of gas flow is superimposed around the pin electrode 108 and through one or more holes 114 in the grid electrode 112, this resulting cloud of charges is swept along with the neutral gas molecules through the grid electrode 112, toward the exit region 119 of the ionizer device 100. It is to be appreciated that there are losses in the ion population due to recombination (e.g. an electron combining with a positive ion to produce a neutral molecule) and charge loss to conducting surfaces such as the grid electrode 112. Nevertheless, the gas flowing 102 through the hole(s) 114 in the grid electrode 112 is generally a mixture of neutral molecules, positive ions and negative ions. This mixture 300 can then be used as the input to an ion separation stage 302 (such as a FAIMS filter or IMS drift tube) followed by a detection stage 304, to produce a tunable chemical detector 306.

It is to be understood and appreciated that gas discharge can be unstable and as a result of this prior art corona systems have utilized a method of limiting the potential for the corona to arc which can damage and prematurely age the corona electrodes. Typically, this control was accomplished via closed loop control, a large series resistor in the case of DC corona, a dielectric barrier covering one electrode (to stop an arc forming) or the use of very high frequency RF (where the time of each cycle is insufficient for an arc to form).

It is to be appreciated the present invention restricts the pin electrode 108 to grid voltage 112 by configuring the corona geometry to be stable thus enabling the use of an open loop which does not obstruct the corona current directly. The threshold voltage is periodically found by using the FAIMS system or other suitable spectrometers or sensors (such as those disclosed in U.S. Patent Application Nos.: 2011/056371 and 2008/017791, each of which is hereby incorporated by reference in its entirety) to detect the threshold (as measuring the AC corona current is difficult in a low-cost and low-power device). It is noted that the pin electrode 108 to grid electrode 112 geometry provides a significant electric field gradient (i.e. stable corona region) and this in turn enables the use of relatively large radius pin electrodes 110 which are more geometrically stable in the aggressive corona environment. A larger radius pin electrode provides a larger ionization volume, which is beneficial for coupling ions out of the ionizer. Additionally, a larger radius pin electrode provides a more uniform electric field thereby avoiding very high peak fields, which can lead to undesirable byproduct formation.

Continuous Positive and Negative Ion Generation

As explained above, the instantaneous ion flow from a corona discharge ionizer consists of ions of one sign—either positive or negative depending on the polarity of the pin electrode. Because ions are generated very close to the pin electrode and because the electric field in the vicinity of the pin electrode is very strong and becomes stronger as the surface of the pin electrode is approached, ions that have the opposite polarity to the pin electrode will not escape the ionization region with their charge intact. Thus, a DC corona discharge ionizer will produce useful ions of only one polarity at a given time.

In ion-based chemical detection systems, useful information is generally contained in the signatures of both positive and negative ions in the gas mixture. Therefore it is useful to have an ion source that can generate ions of both signs. This is the case for both radioactive ion sources and UV ion sources, as neither relies on a strong electrostatic field for ion generation.

In accordance with an illustrated embodiment of the present invention, the corona discharge source uses a high-frequency alternating electric field for ion generation, generating rapid alternating cycle of useful positive and negative ion generation. At typical data sampling frequencies for chemical spectrometers, the effects of these rapid alternations are averaged out whereby the AC corona source behaves essentially as a continuous source of both positive and negative ions. Therefore a single corona ion-source and power supply provides generation of chemical spectra in both positive and negative ion modes. It also eases detection system design constraints as the AC corona source can, in this respect, serve as a drop-in replacement for other continuous ion sources such as radioactive or UV-based ionizers.

It is mentioned some prior art corona-based ionizers use a pulsed configuration, in which ions are generated in short bursts, as the corona drive signal is pulsed. The AC corona source in accordance with the present invention has an advantage over these arrangements as it allows essentially continuous ion generation. It is to be appreciated a continuous stream of ions is useful for the operation of tunable-filter-type chemical spectrometers such as those based on FAIMS. Further, continuous generation of positive and negative ions is also advantageous in ion based analytical systems because the simultaneous presence of both polarities can reduce or eliminate the accumulation of charges on surfaces along the flow path. Charge accumulation on flow path surfaces is generally an undesirable effect that adversely affects performance. The presence of both ion polarities tends to discharge accumulations of charge that would otherwise form, especially when the polarities are in more balanced proportions.

Transfer of Reactant to Product Ions for Both Positive and Negative Ions

Ion mobility detection techniques often rely on a process known as Atmospheric Pressure Chemical Ionization (APCI) to produce the ion population for analysis. In this process, the ion source produces primary ions, known as reactant ions, from the carrier gas (often air). These ions interact with the gas mixture through collisions and charge transfer to produce secondary ions known as product ions. It is often the product ions that are useful in chemical detection. In applications involving the detection of low-level contaminants in a carrier gas, the probability of direct ionization of the contaminant molecules is often very low. However, the process of APCI can result in the transfer of significant amounts of charge to the contaminant molecules, giving enough product ions to form a detectable signal. This process relies on the reactant ions being able to give up their charge to contaminant molecules by collisional interactions. However, positive reactant ions should have relatively low proton affinities and negative reactant ions should have relatively low electron affinities. It is noted many corona-based ionizers are not capable of generating sufficient numbers of negative ions with low-enough electron affinities to give up their charge to contaminants in the carrier gas. For applications involving detection of impurities in air, existing corona-based systems will often respond in the negative ion mode only to the air itself and to byproducts formed from the air by the corona discharge. Thus, this strong response to the carrier gas can mask contaminants that would otherwise appear in the negative ion mode. It is noted reactant ions with very high electron affinities that are often produced in negative coronas include $NO_2^-$ and $NO_3^-$.

For efficient detection of many trace contaminants in the negative ion mode, it is often desirable to generate large quantities of $O_2^-$ ions. It is to be understood and appreciated that the corona ionizer is able to generate significant quantities of $O_2^-$ ions such that the ionizer produces significant quantities of low-electron-affinity negative-mode ions. Therefore, providing the ability to produce strong negative-mode responses from a continuous corona discharge source is a unique and novel aspect of the present invention ionizer. For instance, this is advantageous in that it is particularly useful in the detection of certain chemicals including a number of toxic industrial chemicals, explosives and chemical warfare agents.

Control Methodology to Ensure Consistent Ion Chemistry

It is to be understood and appreciated that the mix of output ions from the present invention ionizer is a function of corona drive voltage, especially for the negative ions. In brief, using drive voltages close to the corona threshold voltage (the lowest voltage at which the discharge is self-sustaining), a significant number of beneficial $O_2^-$ ions are produced. As the drive voltage increases, the proportion of $O_2^-$ ions typically rapidly decreases, being replaced by $NO_2^-$, $NO_3^-$ and other ion species with high electron affinities. Thus, the present invention ionizer performs optimally, especially in the negative mode, when operated close to the corona threshold voltage. It is noted that the drive voltage preferably should be adjusted between 10% and 30% above the threshold to ensure stable ion output.

It is further noted that the threshold voltage for corona discharge is a function not only of electrode geometry, but also of environmental parameters including pressure and temperature. It is to be appreciated the corona threshold voltage is typically proportional to the square root of gas pressure and inversely proportional to the square root of gas temperature. To ensure optimal operation of the ionizer, an illustrated embodiment of the present invention uses a method for adjusting the corona control voltage as follows (and which is not to be understood to be the only method for doing so):

1. Establish the corona threshold voltage (switch-off voltage), $V_{th}$, at a known temperature $T_0$ and pressure $P_0$,
2. During operation of the detector periodically measure the actual temperature T and pressure P in or close to the corona region; and 3. Set the drive voltage of the corona ionizer to a value equal to $A \times V_{th} \times \sqrt{PT_0/P_0T}$, where A is a pre-determined constant, generally in the range 1.1 to 1.3.

The above illustrated and exemplary method ensures that the ionizer is operated in a way that provides a relatively constant and optimal mix of reactant ions for chemical detection in both ion modes. The above describes one preferred embodiment and is not to be understood to be limited thereto.

Fine-Tuning of Corona for in-Service Compensation for Electrode Ageing and Environmental Effects It is to be understood that over the lifetime of a corona ionizer, its threshold voltage will slowly change due to erosion and oxidation of the electrodes. Typically, the pin electrode is repeatedly bombarded by high-energy charged particles, which cause local heating and ejection and redeposition of material from the tip (sputtering). This changes the shape of the tip of the pin electrode and thus alters the electric field profile surrounding it. By-products from reactions between the corona discharge and the carrier gas as well as chemicals deliberately or accidentally introduced to the system can cause chemical changes to the electrodes, such as oxidation. Additionally, effects such as humidity will affect threshold performance of the pin electrode.

Therefore, these effects combine to produce a shift (generally an increase) in the threshold voltage of the device over its service lifetime. In accordance with an illustrated embodiment of the present invention, an exemplary method for compensation can be employed when the ionizer is switched off, as follows:

1. Starting from the "on" state of the ionizer, step the drive voltage down in small decrements while monitoring the ion current output from the ionizer;
2. Record the voltage at which the ionizer switches off during this ramp-down—i.e. the first voltage at which there is no measurable ion current output in either ion mode;
3. Record the pressure and temperature of the gas in or close to the ionizing region at the point when switch-off occurred; and
4. Use these recorded values as the new values of $V_{th}$, $P_0$ and $T_0$ for the system.

Therefore, employing regular re-calculation of the threshold voltage, the ion chemistry and output intensity of the source can be kept more constant over the lifetime of the electrodes.

Alternative Pin Design for Stable Operation

An alternative pin electrode design to that shown in the illustrated embodiment of FIG. 1, which will maintain a more stable radius as it ages, is to use the tip of a narrow wire (for example 0.1 mm diameter). After a short 'burn-in' period the radius of the end of the wire will remain essentially unchanged as the wire is eroded. If necessary this fine wire can be mounted on or fabricated as part of a wider diameter 'pin' for ease of mounting.

Low Duty Cycle Operation for Power Management

It is to be appreciated a key feature of a miniature FAIMS system is a fast response time which combined with low duty cycle operation can reduce power consumption without compromising response time. In an illustrated embodiment of the present invention, and when in low duty-cycle mode, the corona ionizer, gas pump and FAIMS filter driver circuitry are preferably operated in short bursts—each burst of operation preferably being sufficient to take one or more FAIMS spectra. Thus, the present invention ionizer is capable of acquiring a pair of ion sweeps (one positive-mode, one negative-mode) in approximately two seconds. This fast data acquisition time allows very low duty-cycle (and hence low average power) operation without undue compromises in response time. It is noted low-duty-cycle operation relies upon prompt and repeatable initiation of the corona. Exemplary approaches to facilitate this are described below.

Simple UV-Assist Arrangement for Consistent, Fast Initiation

It is to be appreciated an ion source for use in a chemical detection system or for other applications should have the ability to switch on and start generating ions within a known, predictable time period. In many applications there is a need to use the ionizer conservatively, for example to conserve system power in a battery-powered chemical detector. In these situations it is typically important that the ionizer should switch on and produce a stable stream of ions preferably in a short time after voltage is applied to the electrodes. It is noted to be robustly able to initiate corona at low field, over a wide range of humidities and after long periods of standby, a small amount of seed ions is created which results in robust corona initiation.

It is recognized there are many methods of creating UV light with an energy high enough to liberate electrons from a surface via the photoelectric effect or to ionize gas molecules directly. Such methods include using UV LEDs and other methods using gas discharge bulbs. However, in accordance with an illustrated embodiment of the present invention a capacitively coupled low pressure gas discharge lamp (e.g. Hereaus PKR-106) having a UV-transmissive window is used wherein the gas discharge lamp is mounted close to the corona region to allow the corona drive electronics to generate a sufficient electric field in the vicinity of the gas discharge lamp to drive the gas discharge lamp. This enables operation of the UV bulb without the additional cost, size and weight of a separate drive circuit.

Figure 4:
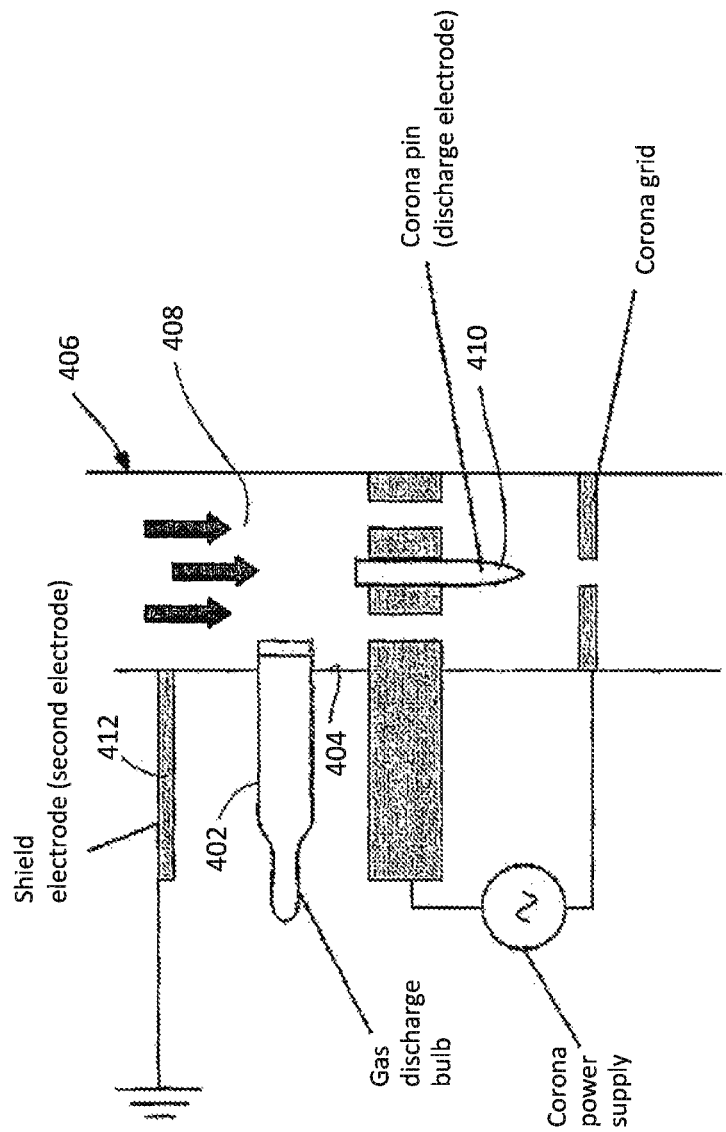
FIG. 4 depicts a cross section of a corona ionizer in accordance with an illustrated embodiment of the invention having UV assistance provided via a low-pressure gas discharge bulb.

An example implementation is shown in FIG. 4. The light source (e.g., bulb) 402 protrudes through the wall 404 of the gas flow pipe 406 so that its UV output illuminates the gas upstream 408 of the corona ionization region. The gas discharge bulb 402 is placed between a high-voltage (pin) electrode 410 and a grounded shield electrode 412. The resultant AC electric field inside the gas discharge bulb 402 causes excitation of molecules, leading to emission of ultraviolet light. It is to be appreciated a purpose of the UV bulb 402 is to generate seed ions, which are very small in number compared with those generated by the corona. This is particularly advantageous in that the performance of the UV initiation system is robust to the precise position of the corona UV bulb 402 and the combined corona/UV-bulb drive voltage. For example no line of sight is required from the bulb to the electrode surfaces. It is to be further appreciated that in additional variations of this illustrated embodiment, UV-created ions are directly detected along with or instead of the corona ions The illustrated embodiment of FIG. 4 relies on a UV source creating seed ions in the system gas flow. It is to be further understood that alternatively, UV light can be used to stimulate photoemission of electrons from a solid surface, such as the corona pin electrode. These electrons, if introduced in to the high-electric field region around the corona pin, will seed avalanche breakdown and initiate the corona discharge. A noted advantage of using photoelectric emission is that the discharge can then be initiated using a lower-energy (longer-wavelength) UV source, such as a UV-light-emitting diode (UV-LED). For instance, an exemplary embodiment using a UV-LED positions the LED so as to illuminate the pin and grid electrode surfaces directly, or through a UV-transmissive optical fiber. It is noted that shining light from a 270 nm UV-LED on to these electrodes is extremely effective at promoting fast, repeatable corona initiation.

Figure 5:
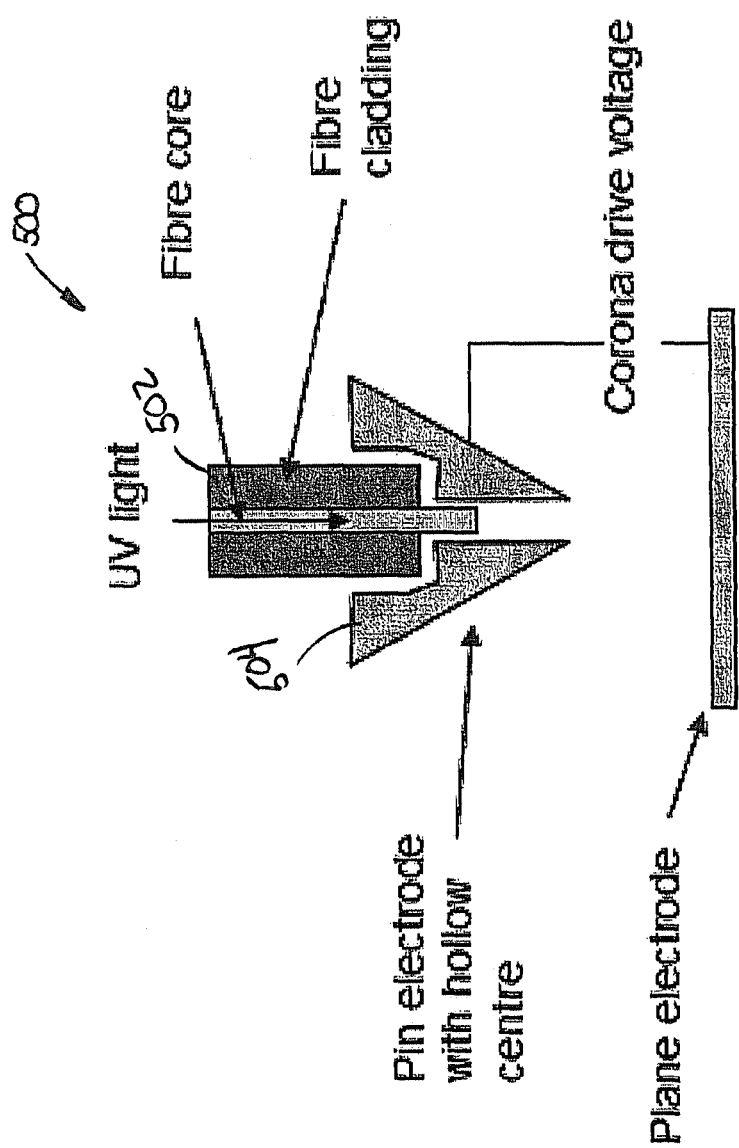
FIGS. 5-7 depict a corona ionizer having UV assistance using an optical fiber in an accordance with illustrated embodiments of the invention.
Figure 6:
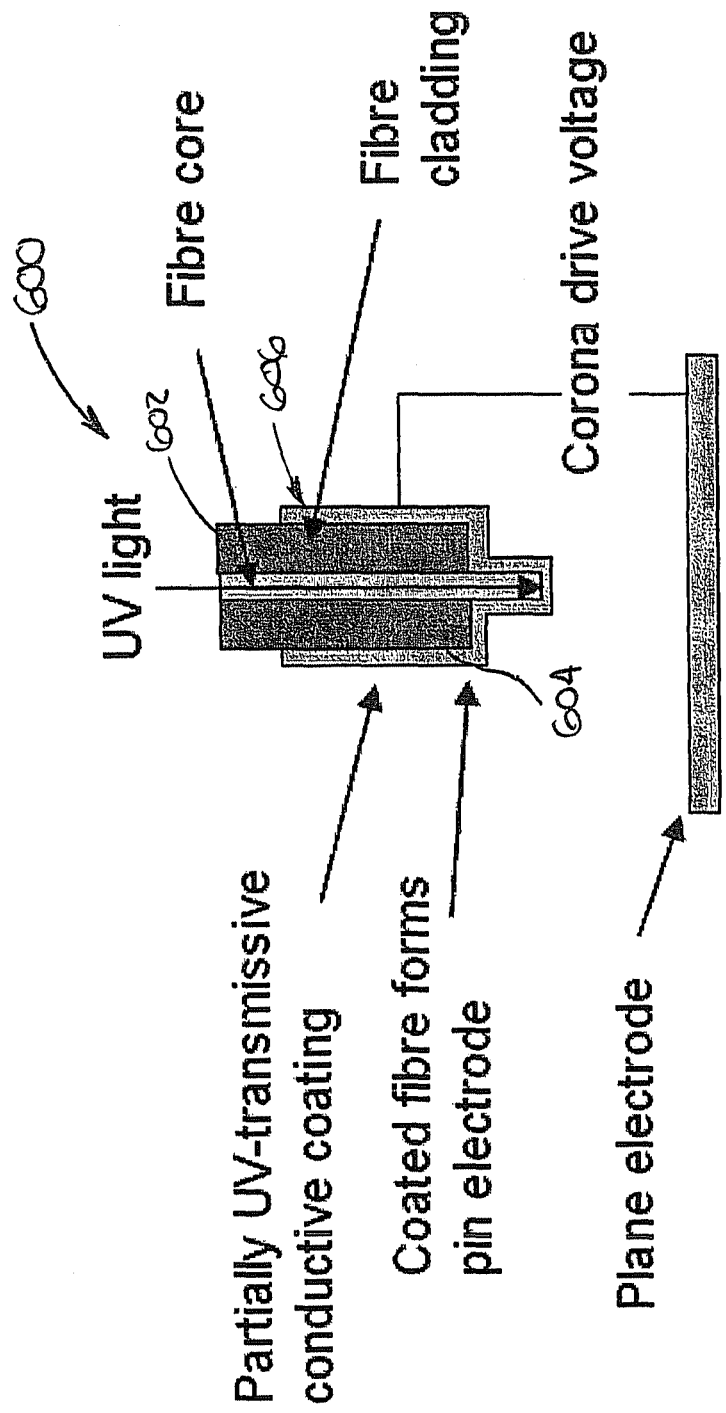

With reference now to FIGS. 5 and 6, yet other illustrated embodiments of discharge devices (500, 600) are shown which preferably use a UV-LED to stimulate photoemission and introduces the UV light using an optical fiber (502, 602). Such a fiber (502, 602) could either be threaded down the core of a hollow pin electrode 504 (FIG. 5) or, if coated with a partially transmissive electrically conductive coating 604, could itself form the pin electrode 606 (FIG. 6).

Figure 7:
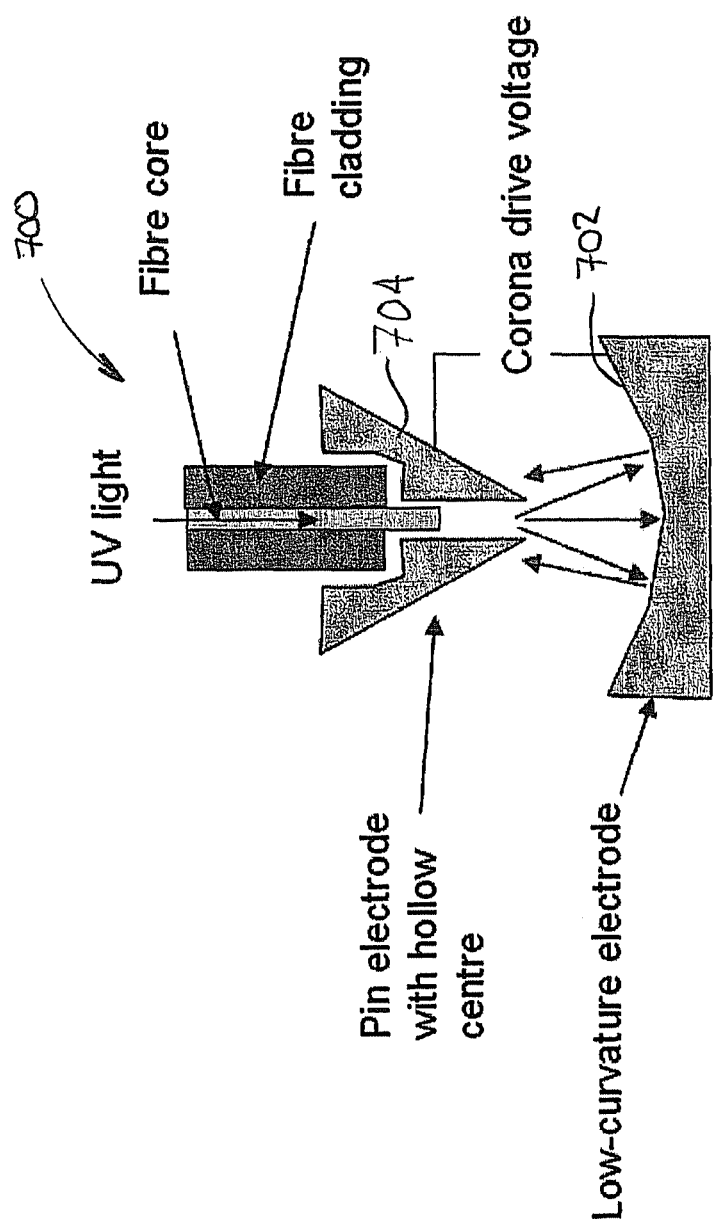

And with reference now to FIG. 7, still another embodiment of a discharge device 700 is illustrated which uses a shaped UV-reflective surface 702, which could also serve as the low-curvature electrode (grid), to direct light back to the sharp electrode 704. It is to be understood that by correctly profiling the reflective surface 702, the UV light intensity at the sharp electrode 704 can be increased thereby increasing the supply of photoelectrons from it. Partial absorption of the UV light at the reflector 702 may also liberate photoelectrons to assist in initiating corona discharge.

Voltage Biasing for Ion Mode Selection

Figure 8:
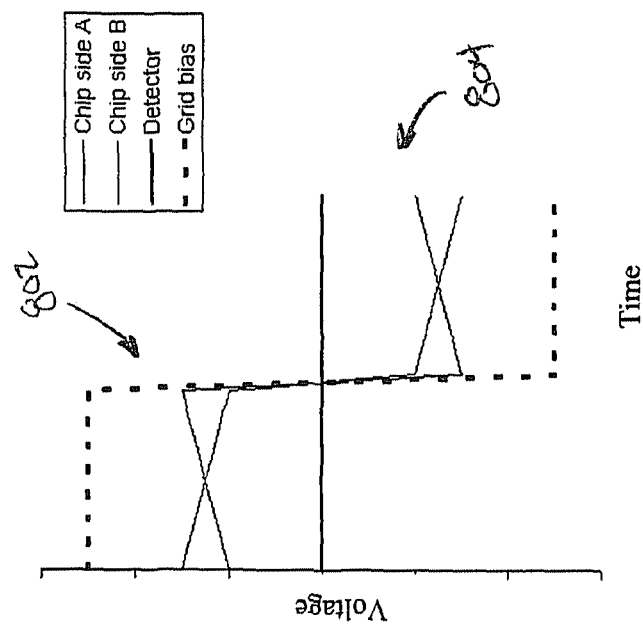
FIG. 8 depicts a corona ionizer as part of a FAIMS chemical detector and a graph illustrating voltages versus time applied to the FAIMS filter and corona ionizer electrode in accordance with the invention for a sequence of positive and negative ion mode sweeps.
Figure 8:
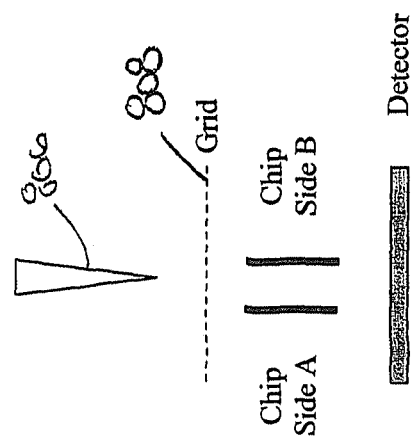

Although the corona discharge source described in this invention is well suited to spectrometer systems filtering and detecting both polarities of ions simultaneously it can also work with sensors analyzing either single ion polarities or alternating between opposing ion polarities sequentially. With reference to FIG. 8, the basic electrode biasing approach is illustrated at exemplary voltage levels with positive mode biasing on the right 802 and negative mode on the left 804. It is noted that the positive 802 and negative 804 mode bias voltages need not be equal and opposite and that they can be set to different values to optimize the system response. It is to be understood that FIG. 8 illustrates one mode of operation with alternating positive and negative mode detection through a single detector. In alternative embodiments it is to be appreciated only a single polarity is detected and yet in other alternative embodiments, simultaneous positive and negative mode detection is achieved using two single polarity detectors operating in parallel.

Capacitive Coupling of Corona Drive Voltage for Ion Mode Equalization

In the biasing scheme described above with reference to FIG. 8, it is noted there is no DC voltage bias applied between the pin electrode 806 and the grid electrode 808. Described herein below is a method of applying a beneficial bias between the pin electrode 806 and the grid electrode 808. In this illustrated embodiment, it is to be understood the ratio of the positive and negative mode ion currents generated by corona discharge is not necessarily equal as it is contingent upon the relative abundance of the positive and negative mode reactant ion peaks and constituent ion mobilities, which depends upon carrier gas and environmental factors such as ambient humidity. A method of improving the ion balance between the positive and negative mode RIPs is to add a capacitor in series with the corona pin.

Figure 9:
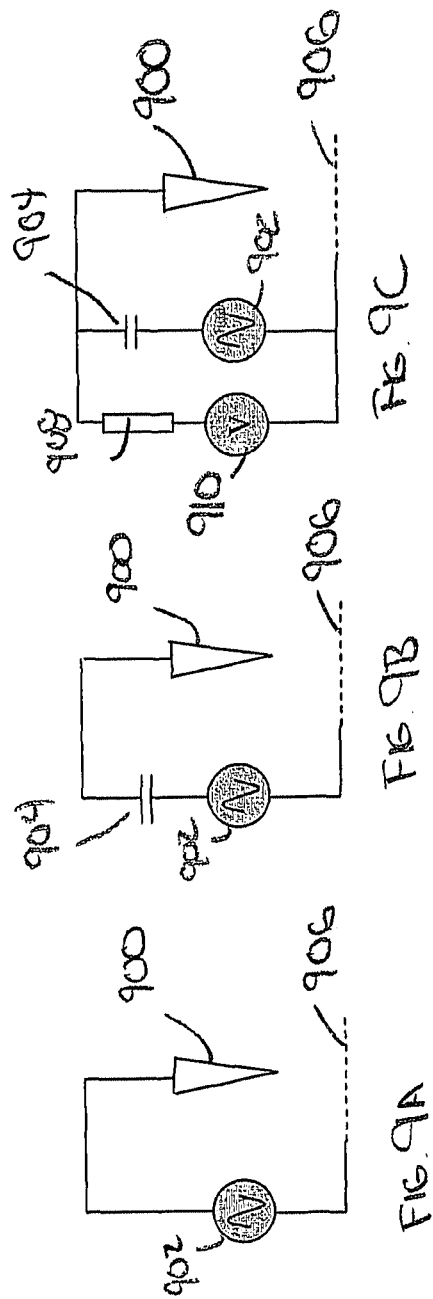
FIGS. 9A-9C, 10A, 10B, 11 and 12 illustrate various alternative embodiments of a corona ionizer in accordance with the invention.

With reference now to FIGS. 9A-9C, FIG. 9A illustrates a pin electrode 900 to grid electrode 906 configuration. FIG. 9B illustrates the pin electrode 900 to grid electrode 906 configuration of FIG. 9A incorporating a series capacitor 904; and FIG. 9C illustrates the pin electrode 900 to grid electrode 906 configuration incorporating a series capacitor 904 of FIG. 9B in parallel with a bias resistor 908 and voltage bias source 910.

Figure 10:
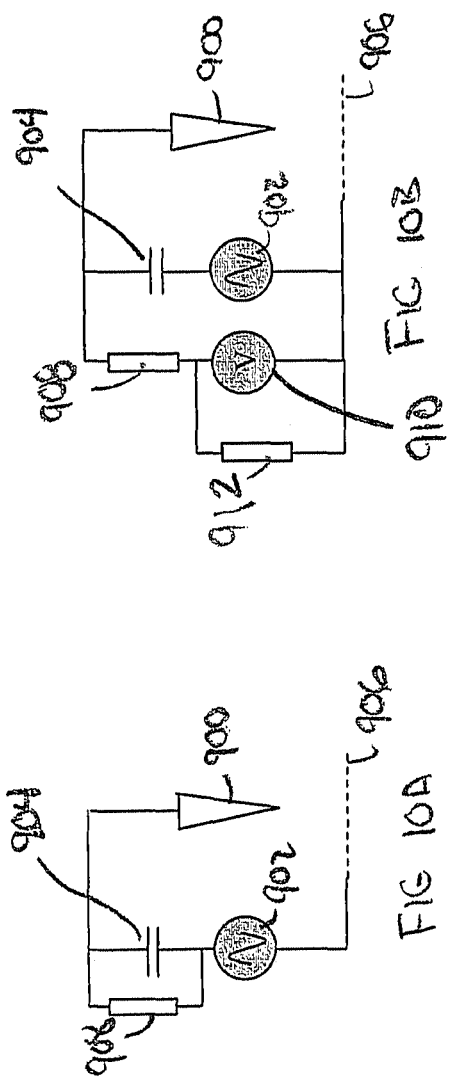

It is to be understood the currents entering the pin electrode 900 from an AC power supply 902 during the two opposing high field regions of the high voltage cycle are equal and opposite in the steady state. Thus, the pin electrode 900 accumulates a DC voltage (superimposed on the AC Corona voltage) that tends to reduce the stronger corona mode and enhances the weaker corona mode. It is to be understood this provides a method of (partially) equalizing the magnitude of the positive and negative ion modes, which advantageously simplifies system operation while reducing byproducts in the negative ion mode. It is to be appreciated a distinction is made between the "drift bias" that builds up on the capacitor 904 and the controlled bias applied between the pin electrode 900 and grid electrode 906. That is, as the capacitor 904 effectively handicaps the stronger mode it affects the corona initiation behavior. For example, in a wet environment (which tends to enhance the positive ion mode) the pin electrode may drift to a bias value that enhances the negative mode spectrum. If the next time the ionizer is used is in a dry environment, this bias value may no longer be appropriate to the operating conditions. As illustrated in FIGS. 10A and 10B, system memory is simply removed by placing a high value resistor 908 across the capacitor 904. This resistor 908 is preferably sized so that in AC operation the current leaking through the resistor 908 has a negligible effect on the pin electrode 900 potential, however when the corona is powered down the potential on the pin electrode 900 will decay over a period of approximately a few seconds. For instance, typical values include one (1) nanofarad for the capacitor 904 and one (1) gigaohm for the resistor 908. Other illustrated embodiments are depicted in FIGS. 10A and 10B, wherein FIG. 10A depicts an ionizer having a pin electrode 900 to grid electrode 906 configuration incorporating a series capacitor 904 and discharge resistor 908 coupled to a power supply, and FIG. 10B depicts an ionizer having a pin electrode 900 to grid electrode 906 configuration of FIG. 10A having a bias resistor 912 and voltage bias source 910 incorporating the discharge resistor 908.

Optimized Corona Grid Geometry for Controlling Ion Chemistry and Ion Mode Balance It is to be appreciated that the present invention corona discharge ionizer in accordance with another illustrated preferred embodiment includes an electrode grid comprising a single central hole having an approximate diameter between 0.25 and 2 mm. However, the present invention corona discharge ionizer is not to be understood to be limited to this configuration, as it may encompass other configurations, whether described herein or not.

It is to be appreciated that the aforesaid single central hole is preferred because ions on the axis of symmetry see no field towards the grid electrode which thus enables some ions to escape from the corona region even during high voltage operation, when ions would normally be swept into the grid electrode. It is further advantageous in that it also facilitates to channel the gas flow through the active corona region at the tip of the pin electrode, thus the corona grid electrode effectively acts as a mobility filter by allowing ions therethrough based on their mobility.

Method of Increasing Charge Equilibration Time

It is to be appreciated that in miniature ionizer systems, as the ion source is moved closer to the ion filter, the charge transferred to the air flow may not have sufficient time to equilibrate with the analyte molecules present in the sample. In other words, there may not be sufficient interaction time for charge to be transferred from the Reactant Ion Peak (RIP) to the Product Ion Peaks (PIPs) by Atmospheric Pressure Chemical Ionization (ACPI). To obviate this occurrence, and in accordance with an illustrated embodiment of the present invention, by increasing the length of time that the charge has to fully equilibrate with the analyte in the air, ion current in the PIPs are improved.

Figure 12:
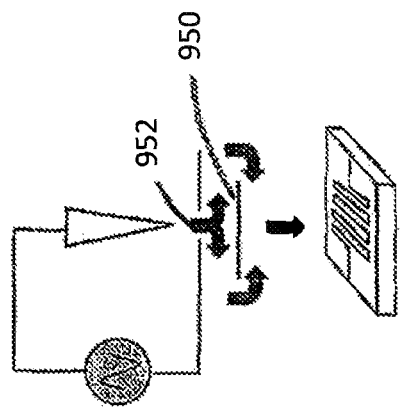
Figure 11:
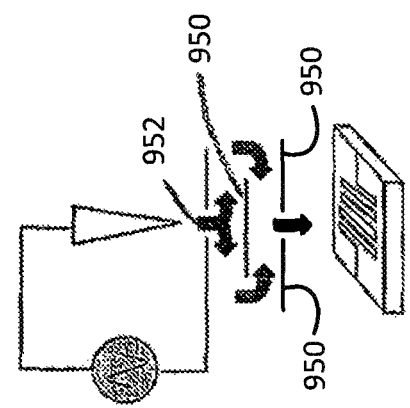

In accordance with an illustrated embodiment of the invention, a method for achieving this is to increase the distance between the grid electrode and the ion filter. In one illustrated method, and particularly where miniaturization is an important parameter, gas flow is diverted through a larger cross sectional area to slow it down and reduce diffusion losses for a given transit time as shown in the illustrated embodiments of FIGS. 11 and 12. Specifically, FIG. 11 depicts baffles 950 in the flow path 952 to extend the transit time between ionization source and ion filter region to improve transfer of charge from RIP to PIP. And FIG. 12 depicts an alternative embodiment to the ionizer shown in FIG. 11 whereby it includes a different number of baffles 952. It is to be understood and appreciated the number of baffles can be increased or decreased to change the flow path length as desired. It is to be further understood and appreciated the baffles 950 may be conducting or non-conducting and, in the case of conducting, may be biased. A preferred embodiment utilizes metallic baffles preferably at the same potential as the grid electrode.

Integrating CDI Elements into Chip Package

Figure 13:
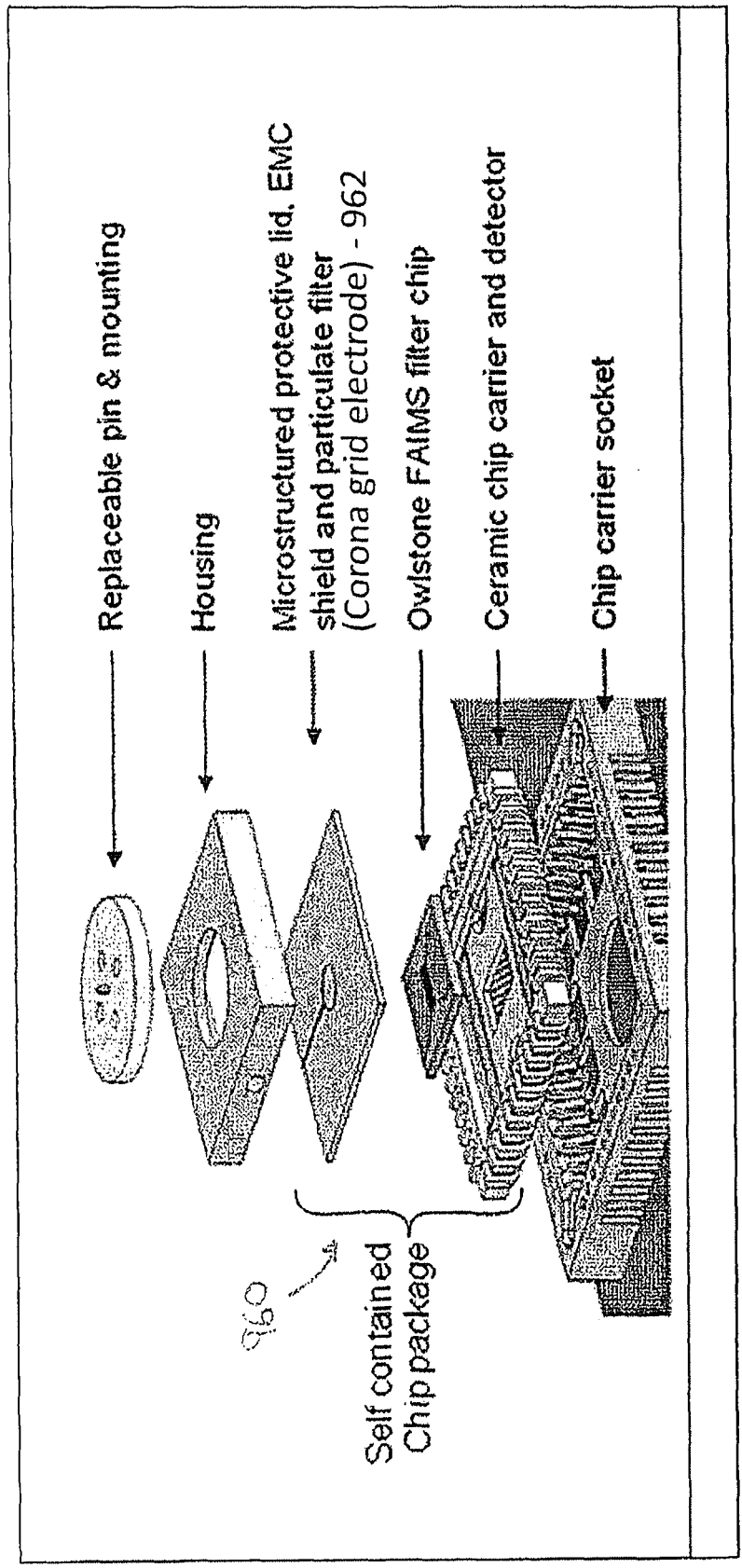
FIG. 13 depicts integration of corona pin and grid alongside a FAIMS chip and detector electrode into an integrated package in accordance with the present invention.

With reference now to the illustrated embodiment of FIG. 13, to further miniaturize a corona-discharge FAIMS system, it is to be understood elements of the corona ionizer are integrated into a chip package 960 (the package that holds the FAIMS filter) which is to be understood to simplify electrical connection to the corona elements. In the illustrated embodiment of FIG. 13, the corona grid electrode 962 is used as a lid for the chip package 960 which is particularly advantageous as it provides a degree of protection to the chip assembly during manufacture while reducing the part count of the assembly.

It is to be understood and appreciated that in an alternative embodiment to that shown FIG. 13, the corona pin electrode and grid electrode are integrated into a single component for compactness, ease of assembly, cost reduction and/or ease of replacement. It is to be further understood and appreciated the integrated pin electrode and grid electrode assembly can be shaped to enable easy installation and replacement after excessive erosion or contamination. The lid of the chip package may be a grid holder as opposed to a grid electrode itself. The chip package may incorporate a detector electrode for instance.

Synchronized Corona Supply

It is noted that FAIMS often requires a sensitive ion current detector and corona ionization can create sources of noise ultimately affecting the signal to noise ratio and detection performance of the system. One approach to obviate this occurrence is to use a shielding device, however this is often difficult in miniature battery powered systems.

In accordance with an illustrated embodiment of the invention, another approach to suppress noise is to synchronize the corona power supply with the ion current sampling clock to ensure that ion current sensing is conducted at a consistent point with respect to the corona power supply output. Another noted advantage of this embodiment is it enables the use of lower frequency corona power supplies which consume less power for a given output voltage.

The above presents a description of a best mode contemplated for carrying out the present invention corona discharge ionizer device, and of the manner and process of making and using the illustrated embodiments, in such full, clear, concise, and exact terms as to enable any person skilled in the art to which it pertains to make and use these devices and methods. The present invention discharge ionizer device is, however, susceptible to modifications and alternative method steps from those discussed above that are fully equivalent. Consequently, the present invention discharge ionizer device is not limited to the particular embodiments disclosed. On the contrary, the present invention discharge ionizer device encompasses all modifications and alternative constructions and methods coming within the spirit and scope of the present invention. Thus, optional embodiments of the present invention discharge ionizer device may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Where a claim, if any, is expressed as a means or step for performing a specified function, it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. An apparatus, comprising:
   a corona discharge ionizer adapted to emit ions generated by corona discharge to a gas flow to be ionized, which includes:
   a discharge electrode having a hollowed body portion;
   a second electrode positioned at a spaced distance from the discharge electrode;
   a power supply coupled to the discharge electrode and the second electrode, the power supply adapted and configured to generate ions in the vicinity of the discharge electrode; and
   an ultraviolet (UV) light source positioned in proximity to the discharge electrode such that UV light is directed through the hollowed body portion whereby the UV light is directed through an optical fiber.

2. The apparatus as recited in claim 1, wherein the power supply is an alternating current (AC) power supply.

3. An apparatus as recited in claim 2, wherein the UV light source is coupled to the AC power supply.

4. An apparatus as recited in claim 2, wherein at least one of the discharge electrode and the second electrode assist in powering the UV source.

5. The apparatus as recited in claim 1, wherein the second electrode is formed from a sheet configured material which has at least one hole formed therein adapted and configured to permit gas flow to pass therethrough.

6. The apparatus as recited in claim 1, wherein the discharge electrode has a pin configured tip portion.

7. The apparatus as recited in claim 1, wherein the UV light source is a lamp.

8. The apparatus as recited in claim 7, wherein the lamp is a gas discharge ultraviolet (UV) lamp.

9. The corona discharge ionizer as recited in claim 1, wherein the UV light source is a light emitting diode (LED).

10. The apparatus as recited in claim 1, wherein the UV light source is a laser.

11. The apparatus as recited in claim 1, wherein the UV light source is adapted to provide direct illumination.

12. An apparatus as recited in claim 1, wherein the optical fiber is provided with a partially UV transmissive conductive coating.

13. An apparatus as recited in claim 12, wherein a portion of the conductive coating forms a pin configured tip portion of the discharge electrode.

14. An apparatus as recited in claim 1, wherein the second electrode has a surface portion adapted and configured to reflect and concentrate UV light onto the discharge electrode.

15. An apparatus as recited in claim 1, wherein the UV light source is adapted to provide illumination in vicinity of at least one of the discharge electrode and the second electrode.

16. An apparatus as recited in claim 1, wherein the UV light source is adapted to provide illumination in an area upstream in the gas flow relative to the discharge electrode and the second electrode.

17. An apparatus as recited in claim 1, further including an additional electrode assembly separate from the discharge electrode and/or the second electrode, the additional electrode assembly coupled to an AC power supply and adapted to assist in powering the UV source.

18. An apparatus as recited in claim 1, wherein the UV light source is coupled to a second power supply separate from the corona discharge power supply.

19. An apparatus as recited in claim 1, further including a tubular structure adapted and configured to direct gas flow therethrough.

20. An apparatus as recited in claim 1, wherein the UV light source is adapted to provide seed ions in the gas flow to assist corona discharge.

21. An apparatus as recited in claim 20, wherein the UV light source is adapted to generate seed ions from the gas flow wherein molecules in the gas flow are ionized by UV light thereby forming at least one of ions and electrons whereby the resulting ions and/or electrons assist with at least one of initiation and sustainment of the corona discharge.

22. An apparatus as recited in claim 20, wherein the UV light source is adapted to generate seed ions via photo-assisted ionization wherein electrons are liberated by UV light from a surface having a work function approximately equal to or less than the photon energy of the UV light causing the emission of electrons into an ambient gas environment whereby the resulting electrons and ions assist with at least one of initiation and sustainment of the corona discharge.

23. An apparatus as recited in claim 22, which further includes a material with a work-function that is lower than the photon energy of the irradiating UV light, adapted and configured to be illuminated by the UV light source, which thereby releases free electrons to assist initiation of ionization.

24. An apparatus as recited in claim 23, wherein the low work-function material forms at least part of at least one of the discharge electrode and the second electrode.

25. An apparatus as recited in claim 1, wherein there is no solid insulating barrier provided intermediate the discharge electrode and the second electrode.

26. An apparatus as recited in claim 1, wherein the corona discharge ionizer is coupled to a spectrometry system.

27. An apparatus as recited in claim 26, wherein the spectrometry system is a Field Asymmetric Ion Mobility Spectrometer (FAIMS).

28. An apparatus as recited in claim 26, wherein the spectrometry system is an Ion Mobility Spectrometer (IMS).

29. An apparatus, comprising:
a corona discharge ionizer adapted to emit ions generated by corona discharge to a gas flow to be ionized, which includes:
a discharge electrode compromising an optical fiber;
a second electrode positioned at a spaced distance from the discharge electrode;
a power supply coupled to the discharge electrode and the second electrode, the power supply adapted and configured to generate ions in the vicinity of the discharge electrode; and
an ultraviolet (UV) light source positioned in proximity to the discharge electrode wherein the UV light is transmitted through the optical fiber.

30. An apparatus as recited in claim 29, wherein the power supply is an alternating current (AC) power supply.

31. The apparatus as recited in claim 30, wherein the UV light source is coupled to the AC power supply.

32. The apparatus as recited in claim 30, wherein at least one of the discharge electrode and the second electrode assist in powering the UV source.

33. An apparatus as recited in claim 29, wherein the second electrode is formed from a sheet configured material which has at least one hole formed therein adapted and configured to permit gas flow to pass therethrough.

34. An apparatus as recited in claim 29, wherein the discharge electrode has a pin configured tip portion.

35. An apparatus as recited in claim 29, wherein the UV light source is a lamp.

36. An apparatus as recited in claim 35, wherein the lamp is a gas discharge ultraviolet (UV) lamp.

37. A corona discharge ionizer as recited in claim 29, wherein the UV light source is a light emitting diode (LED).

38. An apparatus as recited in claim 29, wherein the UV light source is a laser.

39. An apparatus as recited in claim 29, wherein the UV light source is adapted to provide direct illumination.

40. An apparatus as recited in claim 29, wherein the discharge electrode has a hollowed body portion and the UV light is directed through the hollowed body portion.

41. An apparatus as recited in claim 29, wherein the optical fiber is provided with a partially UV transmissive conductive coating.

42. An apparatus as recited in claim 41, wherein a portion of the conductive coating forms a pin configured tip portion of the discharge electrode.

43. The apparatus as recited in claim 29, wherein the second electrode has a surface portion adapted and configured to reflect and concentrate UV light onto the discharge electrode.

44. The apparatus as recited in claim 29, wherein the UV light source is adapted to provide illumination in vicinity of at least one of the discharge electrode and the second electrode.

45. The apparatus as recited in claim 29, wherein the UV light source is adapted to provide illumination in an area upstream in the gas flow relative to the discharge electrode and the second electrode.

46. The apparatus as recited in claim 29, further including an additional electrode assembly separate from the discharge electrode and/or the second electrode, the additional electrode assembly coupled to an AC power supply and adapted to assist in powering the UV source.

47. The apparatus as recited in claim 29, wherein the UV light source is coupled to a second power supply separate from the corona discharge power supply.

48. The apparatus as recited in claim 29, further including a tubular structure adapted and configured to direct gas flow therethrough.

49. The apparatus as recited in claim 29, wherein the UV light source is adapted to provide seed ions in the gas flow to assist corona discharge.

50. The apparatus as recited in claim 49, wherein the UV light source is adapted to generate seed ions from the gas flow wherein molecules in the gas flow are ionized by UV light thereby forming at least one of ions and electrons whereby the resulting ions and/or electrons assist with at least one of initiation and sustainment of the corona discharge.

51. The apparatus as recited in claim 49, wherein the UV light source is adapted to generate seed ions via photo-assisted ionization wherein electrons are liberated by UV light from a surface having a work function approximately equal to or less than the photon energy of the UV light causing the emission of electrons into an ambient gas environment whereby the resulting electrons and ions assist with at least one of initiation and sustainment of the corona discharge.

52. The apparatus as recited in claim 51, which further includes a material with a work-function that is lower than the photon energy of the irradiating UV light, adapted and configured to be illuminated by the UV light source, which thereby releases free electrons to assist initiation of ionization.

53. The apparatus as recited in claim 52, wherein the low work-function material forms at least part of at least one of the discharge electrode and the second electrode.

54. The apparatus as recited in claim 29, wherein there is no solid insulating barrier provided intermediate the discharge electrode and the second electrode.

55. The apparatus as recited in claim 29, wherein the corona discharge ionizer is coupled to a spectrometry system.

56. The apparatus as recited in claim 55, wherein the spectrometry system is a Field Asymmetric Ion Mobility Spectrometer (FAIMS).

57. The apparatus as recited in claim 55, wherein the spectrometry system is an Ion Mobility Spectrometer (IMS).

\* \* \* \* \*